US012753391B2

(12) United States Patent
Matsuzaki et al.

(10) Patent No.: US 12,753,391 B2
(45) Date of Patent: Oct. 6, 2026

(54) HIGH-PURITY MESENCHYMAL STEM CELLS

(71) Applicant: PUREC CO., LTD., Shimane (JP)

(72) Inventors: Yumi Matsuzaki, Shimane (JP); Takashi Suyama, Shimane (JP)

(73) Assignee: PuREC CO., LTD., Shimane (JP)

( * ) Notice: Subject to any disclaimer, the term of this patent is extended or adjusted under 35 U.S.C. 154(b) by 721 days.

(21) Appl. No.: 17/781,676

(22) PCT Filed: Apr. 6, 2020

(86) PCT No.: PCT/JP2020/016228

§ 371 (c)(1),
(2) Date: Jun. 1, 2022

(87) PCT Pub. No.: WO2021/145002

PCT Pub. Date: Jul. 22, 2021

(65) Prior Publication Data

US 2023/0002735 A1 Jan. 5, 2023

(51) Int. Cl.
*C12N 5/0775* (2010.01)

(52) U.S. Cl.
CPC ........ *C12N 5/0663* (2013.01); *C12N 2500/02* (2013.01); *C12N 2501/115* (2013.01)

(58) Field of Classification Search
None
See application file for complete search history.

(56) References Cited

U.S. PATENT DOCUMENTS

| | | | |
|---|---|---|---|
| 2008/0075699 | A1 | 3/2008 | Buhring et al. |
| 2010/0068191 | A1 | 3/2010 | Danilkovich et al. |
| 2011/0053183 | A1 | 3/2011 | Matsuzaki et al. |
| 2017/0204374 | A1 | 7/2017 | Iyoku et al. |

FOREIGN PATENT DOCUMENTS

| | | | |
|---|---|---|---|
| AU | 2015297347 | | 5/2021 |
| EP | 3555265 | B1 | 11/2020 |
| JP | 2012-500214 | A | 1/2012 |
| JP | 6025329 | B2 | 11/2016 |
| JP | 6463029 | B2 | 1/2019 |
| WO | WO 2009/031678 | A1 | 3/2009 |
| WO | WO 2010/019886 | A1 | 2/2010 |
| WO | WO 2016/017795 | A1 | 2/2016 |
| WO | WO 2018/114718 | | 6/2018 |

OTHER PUBLICATIONS

Mabuchi et al (Stem Cell Reports, vol. 1, 152-165, Aug. 6, 2013, Doi: 10.1016/j.stemcr.2013.06.001) (Year: 2013).*
CN Office Action in Chinese Appln. No. 202080078206.X, mailed on Feb. 7, 2024, 12 pages (with English translation).
Lin et al., "Comparison between CD271 and CD133 used for immunomagnetic positive sorting enriching in mesenchymal stem cells from bone marrow," Journal of Experimental Hematology, Apr. 2008, 16(2):333-8 (with English abstract).
CA Office Action in Canadian Appln. No. 3,163,517, dated May 31, 2023, 3 pages.
JP Japanese Office Action in Japanese Appln. No. 2021-570631, dated Apr. 25, 2023, 10 pages (with English translation).
Mabuchi et al., "LNGFR+ THY-1+ VCAM-1hi+ cells reveal functionally distinct subpopulations in mesenchymal stem cells," Stem Cell Reports, Aug. 6, 2013, 1(2):152-65.
PCT International Search Report and Written Opinion in International Appln. No. PCT/JP2020/002197, dated May 19, 2020, 7 pages (with English translation).
PCT International Search Report and Written Opinion in International Appln. No. PCT/JP2020/016228, dated Jun. 30, 2020, 7 pages (with English translation).
PuREC, "Research & Development," May 21, 2017, retrieved May 8, 2020 from URL <https://www.purec.jp/research_and_development/>, 18 pages (with English translation).
Viganò et al., "Tips and tricks for validation of quality control analytical methods in good manufacturing practice mesenchymal stromal cell production," Stem Cells International, Sep. 4, 2018, vol. 2018, 17 pages.
Colter et al., "Identification of a subpopulation of rapidly self-renewing and multipotential adult stem cells in colonies of human marrow stromal cells," Proceedings of the National Academy of Sciences, Jul. 3, 2001, 98(14):7841-5.
EP Extended Search Report in European Appln. No. 20914118.3, dated Dec. 9, 2022, 13 pages.
Siegel et al., "Phenotype, donor age and gender affect function of human bone marrow-derived mesenchymal stromal cells," BMC Medicine, Dec. 2013, 11(1):1-20.
Smith et al., "Isolation of a highly clonogenic and multipotential subfraction of adult stem cells from bone marrow stroma," Stem Cells, Sep. 2004, 22(5):823-31.
AU Office Action in Australian Appln. No. 2020423706, mailed on Jan. 15, 2024, 3 pages.

(Continued)

*Primary Examiner* — Peter Paras, Jr.
*Assistant Examiner* — Khoa Nhat Tran
(74) *Attorney, Agent, or Firm* — Fish & Richardson P.C.

(57) ABSTRACT

A cell population of rapidly proliferating mesenchymal stem cell clones that are positive for LNGFR (CD271) or co-positive for LNGFR (CD271) and Thy-1 (CD90), wherein at least one of the following characteristics (a) and (b) is satisfied. (a) The variation coefficient of forward scattered light in flow cytometry is 35% or less. (b) The average cell size is 20 μm or less.

8 Claims, 6 Drawing Sheets

(56) References Cited

OTHER PUBLICATIONS

IN Hearing Notice in Indian Appln. No. 202217033730, mailed on Oct. 3, 2023, 7 pages.
JP Office Action in Japanese Appln. No. 2021-570631, mailed on Oct. 31, 2023, 8 pages (with English translation).
AU Office Action in Australian Appln. No. 2020423706, mailed on Jul. 11, 2024, 4 pages.
IN Office Action in Indian Appln. No. 202217033730, dated Feb. 27, 2023, 7 pages.
BR Office Action in Brazilian Appln. No. BR112022013344-8, mailed on Feb. 27, 2026, 8 pages (with English translation).
Mabuchi et al., "Supplemental Information: LNGFR+ THY-1+ VCAM-1hi+ cells reveal functionally distinct subpopulations in mesenchymal stem cells," Stem Cell Reports, Aug. 6, 2013, 14 pages.

* cited by examiner

| | FSC CV value | Adipogenic differentiation potential | Proliferation potential | Average cell size (μm) |
|---|---|---|---|---|
| (A) |  |  | 25.0 | 16.9 |
| (B) |  |  | 2.4 | 20.9 |

BM Lot# 18TL158166

| | LT sort | L sort |
|---|---|---|
| Colony | 10.0% | 12.0% |
| REC | 16.7% | 13.0% |
| MEC | 39.6% | 21.7% |
| SEC | 43.8% | 65.2% |

BM Lot# 8F5040

| | LT sort | L sort |
|---|---|---|
| Colony | 8.1% | 9.9% |
| REC | 25.6% | 10.5% |
| MEC | 38.5% | 31.6% |
| SEC | 35.9% | 57.9% |

HIGH-PURITY MESENCHYMAL STEM CELLS

CLAIM OF PRIORITY

The present application is a U.S. National Phase application under 35 U.S.C. § 371 of International Patent Application No. PCT/JP2020/016228, filed on Apr. 6, 2020, which claims the benefit of the priority of International Patent Application No. PCT/JP2020/002197, filed on Jan. 16, 2020. The disclosures of all of the foregoing are incorporated herein by reference in their entirety.

FIELD OF THE INVENTION

The present invention relates to a highly purified homogeneous cell population of rapidly proliferating human mesenchymal stem cells.

BACKGROUND ART

Mesenchymal stem cells (MSCs) are one of the most widely used somatic stem cells, next to hematopoietic stem cells, in clinical practice because of their ability to differentiate into a variety of cell types including bone, cartilage, fat, and the like, with few ethical issues associated with cell collection. Since MSCs can be isolated by a relatively simple procedure, they are widely used as biomaterials, mainly for local transplantation following induction of differentiation into cartilage, bone, or the like in vitro.

For advanced clinical applications, the ability to produce a necessary amount of cells that maintain a certain function is a prerequisite for commercialization.

However, if there are variations in the properties of the starting material (e.g., human bone marrow aspirate), i.e., if there is a difference in the donor-dependent properties, the properties of the cell preparation as a product will be greatly affected.

Therefore, it is important to obtain high-purity mesenchymal stem cells with minimal variation.

The present inventors have isolated LNGFR/Thy-1-double-positive cells from a cerebrospinal fluid by flow cytometry to obtain rapidly expanding clones (RECs), thereby establishing a purification and isolation method that can eliminate the difference in the donor-dependent proliferation potential of the MSCs (Japanese Patent No. 6463029, WO2016/017795, Mabuchi Y. et al, Stem Cell Reports 1(2): 152-165, 2013). According to this method, RECs are isolated and selected, for example, using Ror2 expression as an indicator.

In addition, a purified mesenchymal stem cell composition and a method for purifying a mesenchymal stem cell composition are also known (Japanese Patent No. 6025329). According to this method, mesenchymal stem cells with a diameter of 150 μm or less are purified.

However, variation is still observed in the differentiation potential and the proliferation potential of the REC clones. Moreover, even RECs with excellent proliferation potential will inevitably deteriorate due to repeated passages, and therefore an effective quality control method has been sought. Furthermore, even for the use of Ror2 expression as an indicator, there is room for improvement regarding correlation with the proliferation potential.

PRIOR ART LITERATURE

Patent Literature

Patent literature 1: Japanese Patent No. 6463029

Patent literature 2: International Patent Application Publication WO2016/017795

Patent literature 3: Japanese Patent No. 6025329

Non-Patent Literature

Non-patent literature 1: Y Mabuchi, S Morikawa, S Harada, K Niibe, S Suzuki, F Renault-Mihara, D D Houlihan, C Akazawa, H Okano, Y Matsuzaki, *LNGFR+Thy-1+Vcam-1hi+ cells reveal functionally distinct subpopulations in mesenchymal stem cells*, Stem Cell Reports, 1(2): 152-165, 2013.

SUMMARY OF THE INVENTION

Problem to be Solved by the Invention

Thus, the present invention aims at establishing a method for selecting high-purity and highly homogeneous RECs and an indicator that guarantees the cell performance.

Means for Solving the Problem

The present inventors have investigated to solve the above problem, where cells positive for both LNGFR and Thy-1 were obtained from a human bone marrow aspirate and a number of REC clones were produced from each single cell to measure the differentiation and proliferation potentials of the cells. By repeating this, the present inventors found that the size and uniformity of the cells had stronger correlation with the differentiation and proliferation potentials of each clone.

In addition, the present inventors analyzed the size and variation of the cells constituting each clone using forward scatter (FSC) in flow cytometry as an indicator, and found that the smaller the cell size and the CV value of FSC, the better the proliferation and differentiation potentials, and that cells having functions within a certain range can be produced by selecting the clones based on these indicators.

Thus, the present invention is as follows.

(1) A cell population of rapidly proliferating mesenchymal stem cell clones that are positive for LNGFR (CD271) or that are double-positive for LNGFR (CD271) and Thy-1 (CD90), wherein the cell population satisfies at least one of the following characteristics (a) and (b):

(a) the coefficient of variation of the forward scatter in flow cytometry is 35% or less; and (b) the average cell size is 20 μm or less.

(2) The cell population according to (1), wherein the coefficient of variation is 30% or less.

(3) The cell population according to either one of (1) and (2), wherein the average cell size is 14 μm to 18 μm.

(4) A method for evaluating the quality of a cell population of rapidly proliferating mesenchymal stem cell clones that are positive for LNGFR (CD271) or that are double-positive for LNGFR (CD271) and Thy-1 (CD90), wherein a cell population that satisfies at least one of the following characteristics (a) and (b) is judged to be of a high quality:

(a) the coefficient of variation of the forward scatter in flow cytometry is 35% or less; and (b) the average cell size is 20 μm or less.

(5) The method according to (4), wherein the coefficient of variation is 30% or less.

(6) The method according to either one of (4) and (5), wherein the average cell size is 14 μm to 18 μm.

(7) A method for selecting a clinically applicable cell population from cell populations of rapidly proliferating mesenchymal stem cell clones that are positive for LNGFR (CD271) or that are double-positive for LNGFR (CD271) and Thy-1 (CD90), wherein a cell population that satisfies at least one of the following characteristics (a) and (b) is selected as a population of therapeutic mesenchymal stem cells:

(a) the coefficient of variation of the forward scatter in flow cytometry is 35% or less; and (b) the average cell size is 20 μm or less.

(8) The method according to (7), wherein the coefficient of variation is 30% or less.

(9) The method according to either one of (7) and (8), wherein the average cell size is 14 μm to 18 μm.

SUMMARY OF THE INVENTION

According to the present invention, a mesenchymal stem cell population uniform in cell size and excellent in proliferation potential and differentiation potential can be selected. The selected cell populations have a clinically applicable quality and are expected to be useful for a treatment of myocardial infarction, cerebral infarction, spinal cord injury, bone- or cartilage-formation-related disease, graft-versus-host disease (GVHD), liver cirrhosis, epidermolysis bullosa, lower limb ischemia, and the like.

MODE FOR CARRYING OUT THE INVENTION

Figure 1:
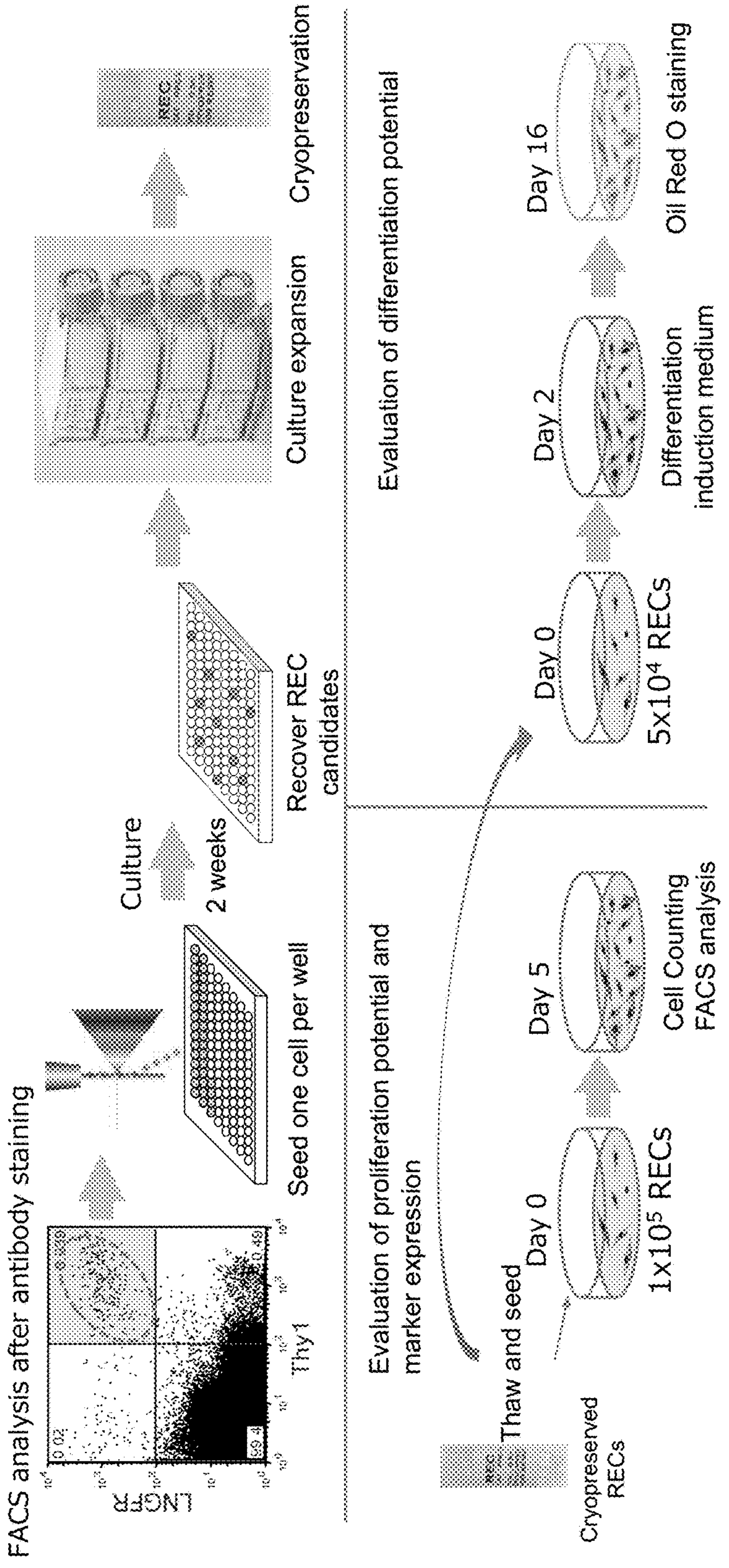
FIG. 1: An overview of a process of selecting RECs according to the present invention.

Hereinafter, the present invention will be described in detail.

1. General

The present inventors have previously succeeded in isolating rapidly expanding clones (RECs) from mesenchymal stem cells that are positive for LNGFR (CD271) (CD271+ cells) and mesenchymal stem cells that are double-positive for LNGFR (CD271) and Thy-1 (CD90) (CD271+CD90+ cells).

These RECs refer to cells that can reach confluence in two weeks when they are seeded and cultured one cell per well in a 96-well plate, and that have all of the proliferation potential, the differentiation potential, and the migration ability 1,000-fold or higher than those of mesenchymal stem cells obtained by conventional methods. Since the RECs particularly retain migration ability, they can be administered intravenously and thus are expected for their application to serious systemic diseases such as skeletal dysplasia.

Even among such REC clones, however, variation in the differentiation and proliferation potentials is sometimes observed.

The present invention provides cell clones with less variation and a method for selecting such cell clones.

A cell population including cell clones of the present invention is a cell population of rapidly proliferating mesenchymal stem cell clones that are double-positive for LNGFR (CD271) and Thy-1 (CD90), wherein the cell population satisfies at least one of the following characteristics (a) and (b):

(a) the coefficient of variation of the forward scatter in flow cytometry is 35% or less; and (b) the average cell size is 20 μm or less.

2. Method for Enriching Human Mesenchymal Stem Cells

According to the present invention, mesenchymal stem cells that are positive for LNGFR (CD271) or that are double-positive for LNGFR (CD271) and Thy-1 (CD90) can be obtained, for example, by following the method described in WO2009/31678.

An overview of this method is as follows.

First, mesenchymal stem cells are highly enriched by sorting out cell fractions that are positive for LNGFR (CD271) (CD271+) or that are double-positive for CD271 and CD90 (CD271+CD90+) from a cell population containing human mesenchymal stem cells. If the cell population containing human mesenchymal stem cells contains hematopoietic cells, a step of sorting out cells that are double-negative for CD45 and CD235a (CD45−CD235a−) can be added to sort out non-hematopoietic cells.

The cell population containing mesenchymal stem cells can be prepared by flow cytometry or affinity chromatography.

While a material used for obtaining this cell population is not limited, examples thereof include bone marrow and peripheral blood (including peripheral blood collected after G-CSF administration). Bone marrow may be collected from the spine, sternum, iliac bone, or the like.

If the material used for cell preparation consists of aggregated spheres including mesenchymal stem cells, the material can be subjected to a mechanical treatment such as pipetting or an enzymatic treatment using trypsin, collagenase, etc., as necessary. Moreover, if the material is contaminated with red blood cells, the red blood cells are preferably hemolyzed in advance.

The cell population prepared as described above is used for sorting out CD271+ cells or CD271+CD90+ cells.

In one exemplary method for sorting out CD271+ cells or CD271+CD90+ cells, antibodies are used.

The antibodies are anti-CD271 and/or anti-CD90 antibodies that are capable of sorting out CD271+ cells or CD271+ CD90+ cells. When flow cytometry is employed for sorting, an anti-CD271 antibody or anti-CD271 and anti-CD90 antibodies labeled with different fluorescent dyes such as FITC, PE, or APC can be used in an appropriate combination to sort live cells in a short time. Other than flow cytometry, CD271+CD90+ cells can also be sorted by a method using magnetic beads or affinity chromatography.

Prior to these methods, dead cells may be removed by allowing the cell population to react with a fluorescent dye (e.g., PI) that stains dead cells and subsequently removing the fluorescently stained cells.

3. Enriching REC Cells

Next, single-cell culturing (cloning) of the sorted LNGFR-positive cells or LNGFR- and Thy1-double-positive cells is performed to select a lot of rapidly proliferating cells, thereby obtaining high-purity human mesenchymal stem cells (REC: Rapidly Expanding Clones) excellent in proliferation potential, differentiation potential, and migration ability.

FIG. 1 illustrates a process of isolating the RECs by single-cell cloning.

Mononuclear cells are prepared from human bone marrow or fat/placental chorion, and the bone marrow mononuclear cells are stained using anti-LNGFR antibody alone or anti-LNGFR and anti-Thy1 antibodies. Then, using flow cytometry (cell sorter), LNGFR-positive cells or LNGFR- and Thy1-positive cells are cloned and sorted into a 96-well culture plate. Specifically, one cell per well is seeded. After 2 weeks of single-cell culturing, an image of the culture plate is photographed under a microscope select wells that are confluent or semi-confluent and designate cells contained in these wells as RECs.

Herein, "rapidly proliferating" and "rapidly expanding" mean that, when one cell per well is seeded and cultured in a 96-well culture plate, the growth rate is such that the culture plate becomes confluent or semi-confluent within two weeks of culture (doubling time of 26±1 hour).

Confluent refers to a state where 90% or more of the surface of a culture container (surface of the culture) is covered by cultured cells. In addition, semi-confluent refers to a state where 70-90% of the surface of a culture container (surface of the culture) is covered by cultured cells. The size and type of the culture equipment used can be changed as appropriate depending on the growth rate of the cells. Cells that proliferate later on (moderately or slowly expanding cells), i.e., cells that are not semi-confluent or confluent after 2 weeks of single-cell culturing, are discarded. The RECs collected from each of the selected wells are transferred to a culture flask for each well and further cultured to confluency (expansion culture). The cells from the expanded culture are then collected separately. RECs from one well are considered one lot and will be used for the selection described below.

Since the cells of the present invention are obtained by cloning and selection where one cell is seeded per well, the genetic traits among all of the expanded cells are identical. Therefore, according to the present invention, the entire cell population may be referred to as a "clone" or each of the cells constituting the cell population may be referred to as a "clone".

According to the present invention, RECs used for selecting can also be evaluated in advance using an REC marker (anti-Ror2). For example, after the aforementioned expanding culture, proliferating adherent cells are collected from all lots, and a portion (about 1 to $3\times10^5$ cells) of each lot is stained with an anti-Ror2 monoclonal antibody for single staining. A technique of single staining using an anti-Ror2 monoclonal antibody is known (WO2016/17795). Briefly, the percentage of REC marker-positive cells in the collected cells is determined by flow cytometry analysis using an REC marker. The percentage can be determined by quantitating Ror2 mRNA expression using quantitative PCR, or can be determined manually by microscopy. Lots (cell populations) having a certain percentage of positive cells (e.g., 65%) are considered acceptable and will be used for the selecting described below.

4. Selecting Stem Cell Population of the Invention

The present invention is capable of selecting high-purity RECs with better cell performance by examining the proliferation potential and adipogenic differentiation potential of the cells, the expression level of an REC-specific marker, and the uniformity of the cell size for each lot of REC clones and analyzing the correlation between them.

In the present invention, the coefficient of variation (CV value) of the forward scatter and the average cell size are used as the indicators for selecting.

Forward scatter is light that is scattered at a small angle in the forward direction relative to the axis of the laser beam. Forward scatter consists of scattered, diffracted, and refracted laser light produced at the cell surface and provides information about the size of the sample.

The coefficient of variation (CV) is the standard deviation divided by the mean, and is a value used to relatively evaluate the variability of data set in different units and the relationship between data and variability with respect to the mean.

According to the present invention, cell populations are selected for those with a CV value of 35% or less. A cell population with a CV value of 35% or less is a cell population composed of cells that are uniform in size. Preferably, the CV value is 30% or less, 25% or less, or 20% or less.

Furthermore, the average size of the cells in the cell population selected by the present invention is 20 μm or less. The average size of the cells is preferably 18 μm or less, and in a range of 14 μm to 18 μm.

The present invention also provides a method for evaluating the quality of a cell population of rapidly proliferating mesenchymal stem cell clones that are positive for LNGFR (CD271) or that are double-positive for LNGFR (CD271) and Thy-1 (CD90). According to the present invention, a cell population that satisfies at least one, preferably both, of the following characteristics (a) and (b) is judged to be of a high quality:

(a) the coefficient of variation of the forward scatter in flow cytometry is 35% or less; and
(b) the average cell size is 20 μm or less.

The cell population evaluated and selected in this manner is not limited in the number of cell clones that make up the population, and may have, for example, about $0.8\times10^7$ to $1.2\times10^7$ cells in 1 ml of solution.

The cell population is also clinically applicable as a therapeutic mesenchymal stem cell population for treating diseases including, but not limited to, the followings.

Genetic disorders (epidermolysis bullosa, hypophosphatasia, etc.).

Bone and joint diseases (knee cartilage defect, knee osteoarthritis, spinal disc herniation, etc.).

Cardiac diseases (myocardial infarction, ischemic heart failure, etc.).

Liver diseases (liver cirrhosis, non-alcoholic steatohepatitis, etc.).

EXAMPLES

Hereinafter, the present invention will be described further in detail by way of examples. The scope of the invention, however, should not be limited to these examples.

Example 1

1. Determining CV Value of Forward Scatter (FSC) in Flow Cytometry.

REC clones (clone numbers: 1-45), prepared beforehand by a known method (WO2016/17795) and the scheme shown in FIG. 1, were used for determining the CV value of forward scatter in flow cytometry.

Figure 2:
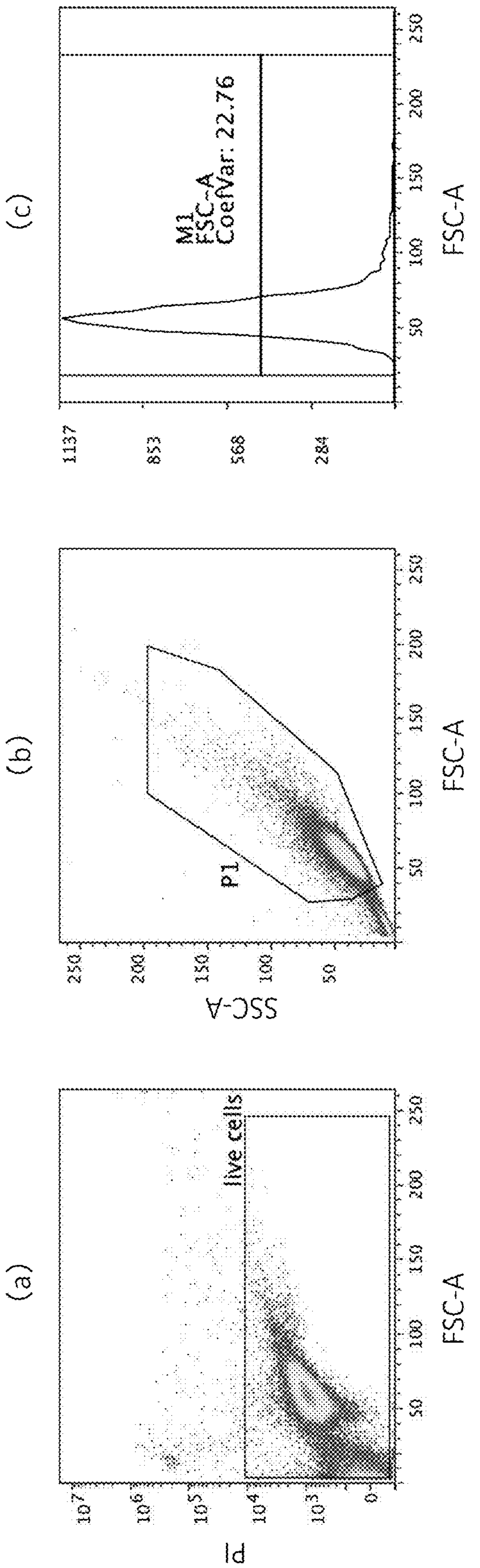
FIG. 2: A result of determining a CV value of forward scatter (FSC) in flow cytometry.

FSC in flow cytometry is proportional to the surface area or size of the cell. In this example, the variation in cell size was evaluated using the CV value of FSC as an indicator. FIG. 2 shows a result of determining a CV value of forward scatter (FSC) in flow cytometry.

(a) PI staining was performed on individual REC clones, and dead cells were excluded from the analysis by setting a gate for PI-negative live cell population.

(b) The PI-negative live cell population was plotted on an FSC/SSC cytogram, where a gate (P1) was set for the main cell population to exclude debris and noise from the analysis.

(c) The cell population within the P1 gate was plotted on an FSC histogram, and a marker (M1) was placed to determine the CV value.

Figure 3:
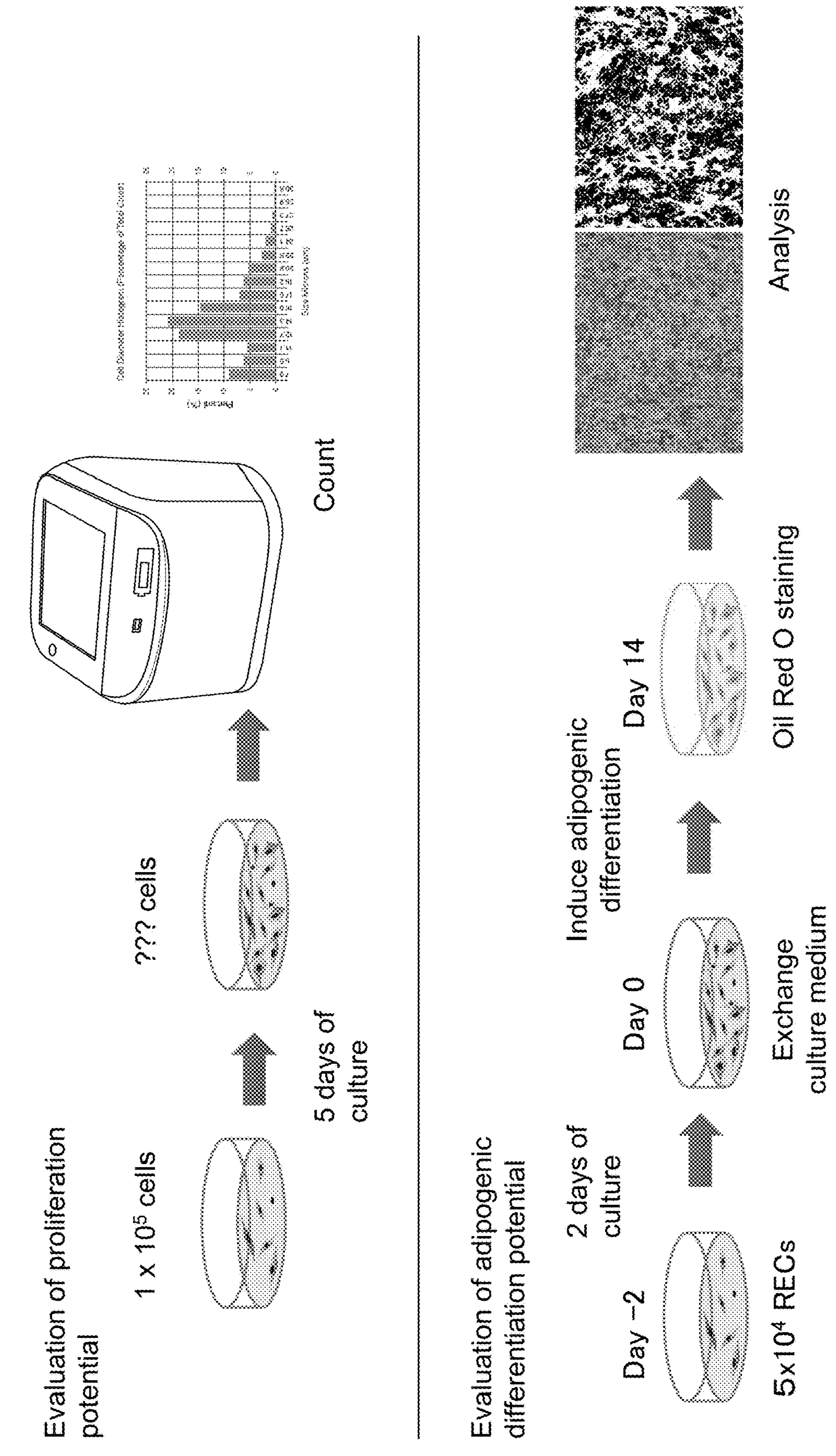
FIG. 3: Results of evaluating cell proliferation potential and adipogenic differentiation potential.

2. Evaluating Cell Proliferation Potential and Adipogenic Differentiation Potential (FIG. 3)

(1) Method for Evaluating Cell Proliferation Potential $1 \times 10^5$ REC cells were seeded in a 100 mm culture dish and cultured for 5 days at 37° C. in a 5% $CO_2$ environment, after which the cell count and the average cell size were determined using a cell counter. As the culture medium, a DMEM medium (Fujifilm Wako Pure Chemical Corporation) supplemented with FBS, basic FGF, Hepes, and penicillin-streptomycin was used.

(2) Method for Evaluating Adipogenic Differentiation Potential $5 \times 10^4$ REC cells were seeded in a 24-well plate and cultured for 2 days at 37° C. in a 5% $CO_2$ environment, and then the medium was replaced with an adipogenic differentiation induction medium to culture the cells for another 14 days. After 14 days of culture, Oil Red O staining was performed and the area of the lipid droplets was determined by image analysis. As the adipogenic differentiation induction medium, the culture medium of (1) further supplemented with Dexamethasone, Indomethacin, and IBMX was used.

3. Exhaustive Analysis

Figure 4:
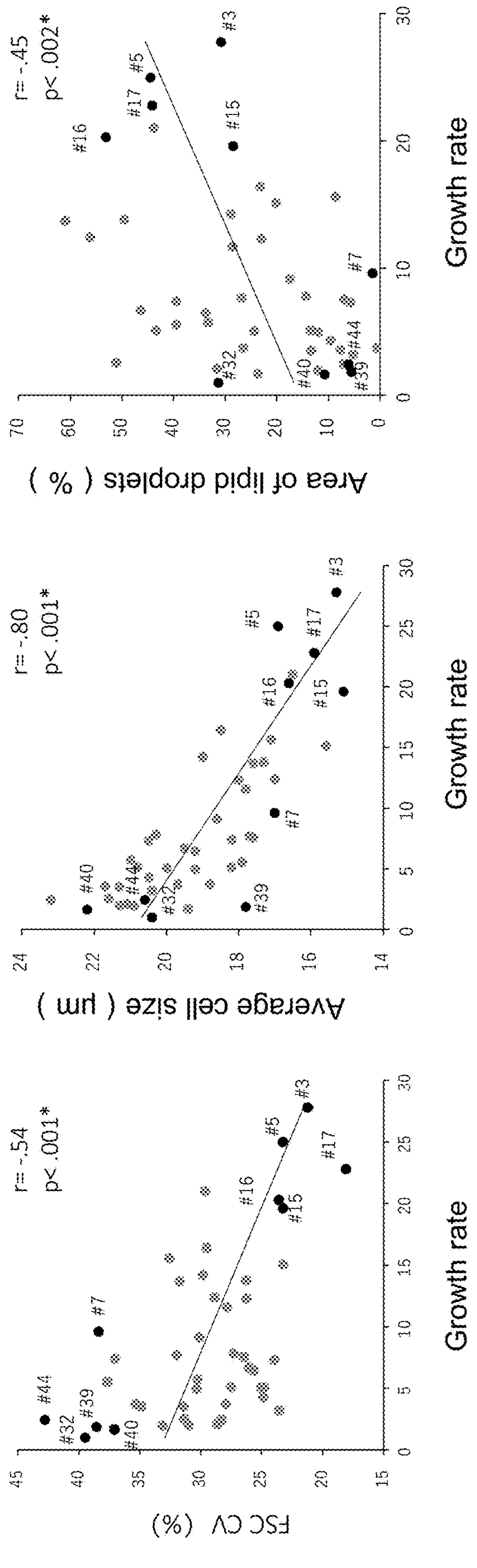
FIG. 4: Results of exhaustive analyses of REC clones.

An exhaustive analysis was performed on the forty-five REC clones obtained after one round of sorting (FIG. 4).

For each REC clone, we examined the CV value of FSC, the cell growth rate (proliferation potential), the average cell size, and the adipogenic differentiation potential, and found that REC clones (#3, #5, #15, #16, and #17) with lower CV values of FSC had higher proliferation and differentiation potentials and smaller average cell sizes.

On the other hand, REC clones (#7, #32, #39, #40, and #44) with higher FSC CV values showed lower proliferation and differentiation potentials and larger average cell sizes.

The average growth rate of clones with a CV value of 30% to 35% was 6.4, the average growth rate of clones with a CV value of 25% to 30% was 9.2, and the average growth rate of clones with a CV value of 25% or less was 15.1. Meanwhile, the average growth rate of clones with an average cell size of 18 to 20 μm was 7.0, the average growth rate of clones with an average cell size of 16 to 18 μm was 12.7, and the average growth rate of clones with an average cell size of 16 μm or less was 21.3.

These results show that high-quality REC clones having both high proliferation potential and high differentiation potential can be selected using the CV value of FSC and the average cell size as indicators.

Figure 5:
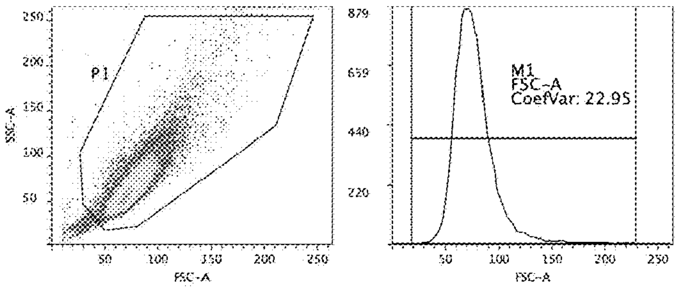
FIG. 5: Summary of the results of the analyses of the present invention.
Figure 5:
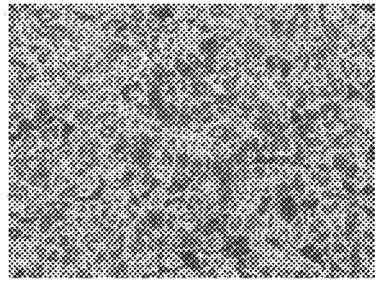
Figure 5:
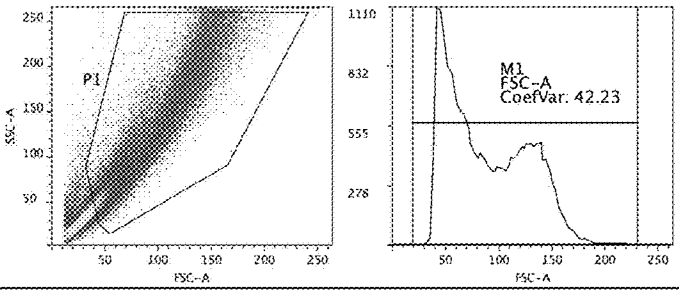
Figure 5:
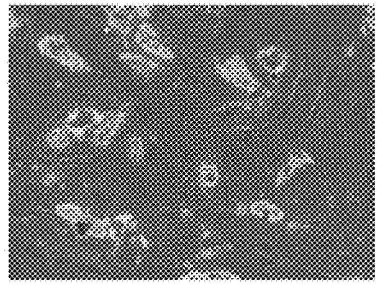

4. Summary of Typical Examples that were Analyzed (FIG. 5)

Clone A, with a low FSC CV value and a small average cell size, is a high-quality REC clone having high adipogenic differentiation potential and high proliferation potential.

Clone B, with a high FSC CV value and a large average cell size, is a substandard REC clone having low adipogenic differentiation potential and low proliferation potential.

Example 2

Figure 6:
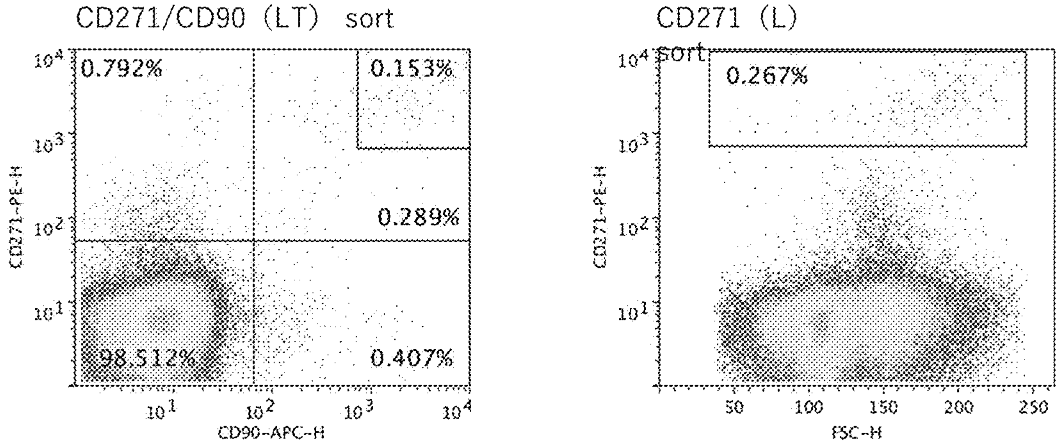
FIG. 6: Results of exhaustive analyses of REC clones.
Figure 6:
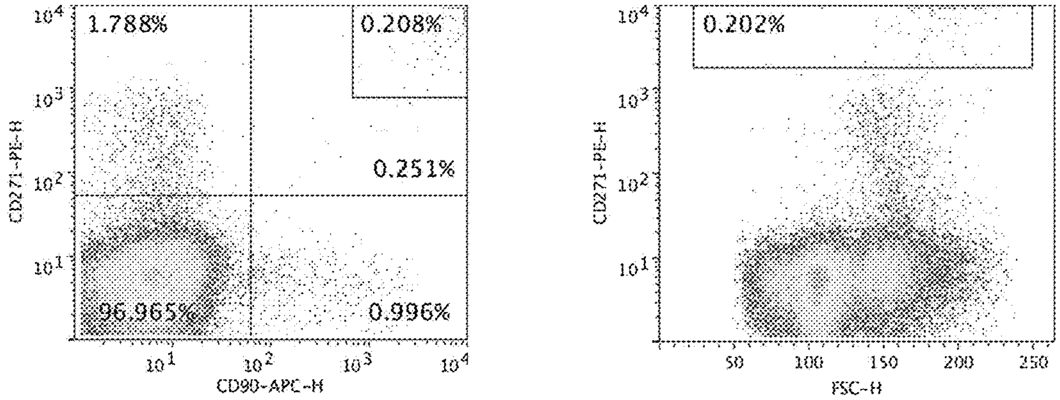

Two kinds of bone marrow aspirate lots (#18TL158166 and #8F5040) were sorted by two methods (double-positivity for CD271 and CD90 or positivity for CD271 alone) and the percentages of the resulting colonies, RECs, MECs, and SECs were compared (FIG. 6).

In FIG. 6, the left panel shows the results from cell sorting. The cells in the boxed areas were seeded into 96-well plates and the percentages of the obtained colonies are shown in the row "Colony" of the table on the right. The percentages of rapidly expanding colony (REC), moderately expanding colony (MEC), and slowly expanding colony (SEC) among the obtained colonies are shown in the table.

Compared to sorting using double-positivity for LNGFR and CD90 as an indicator, sorting using positivity for LNGFR alone yielded a higher percentage of colonies, but a lower percentage of RECs.

However, RECs were found to be isolatable even when they were sorted using positivity for LNGFR alone.

The invention claimed is:

1. A cell population of rapidly proliferating mesenchymal stem cell clones that are positive for LNGFR (CD271) or that are double-positive for LNGFR (CD271) and Thy-1 (CD90), wherein the average cell diameter is 20 μm or less and the coefficient of variation of the forward scatter of the cell population in flow cytometry is 35% or less.

2. The cell population according to claim 1, wherein the coefficient of variation is 30% or less.

3. The cell population according to claim 1, wherein the average cell size is 14 μm to 18 μm.

4. The cell population according to claim 1, wherein the average cell size is 20 μm or less.

5. The cell population according to claim 1, wherein the cell population is obtained by a method comprising:

(a) obtaining mesenchymal stem cell clones that are positive for LNGFR (CD271) or that are double-positive for LNGFR (CD271) and Thy-1 (CD90);

(b) single-cell culturing the mesenchymal stem cell clones; and (c) collecting rapidly expanding clones;

wherein the average cell diameter is 20 μm or less and the coefficient of variation of the forward scatter in flow cytometry of the cell population is 35% or less.

6. A culture of a cell population of human mesenchymal stem cells, wherein the cell population is obtained by a method comprising:

(a) obtaining a cell population of mesenchymal stem cell clones that are positive for LNGFR (CD271) or that are double-positive for LNGFR (CD271) and Thy-1 (CD90);

(b) single-cell culturing the mesenchymal stem cell clones; and (c) collecting rapidly expanding clones;

wherein the average cell diameter is 20 μm or less and the coefficient of variation of the forward scatter in flow cytometry of the culture is 35% or less.

7. The culture according to claim 6, wherein:

(a) the average cell size is 20 μm or less; and/or (b) the coefficient of variation is 30% or less.

8. The culture according to claim 7, wherein the average cell size is 14 μm to 18 μm.

* * * * *